United States Patent [19]

Partridge

[11] 4,119,091
[45] Oct. 10, 1978

[54] TIE FOR USE IN BONE FRACTURE SURGERY

[75] Inventor: Anthony John Partridge, Sussex, Great Britain

[73] Assignee: Chichester Partridge Limited, Sussex, England

[21] Appl. No.: 811,530

[22] Filed: Jun. 30, 1977

[30] Foreign Application Priority Data

Jul. 6, 1976 [GB] United Kingdom ............... 27975/76

[51] Int. Cl.² .......................... A61F 5/04; A61B 17/18
[52] U.S. Cl. ............................... 128/92 B; 128/92 D; 128/92 CA
[58] Field of Search ................. 128/92 B, 92 D, 92 R, 128/92 C, 92 CA, 92 EA, 83, 82

[56] References Cited

U.S. PATENT DOCUMENTS 3,463,148  8/1969  Treace ................................ 128/92 D
3,469,573  9/1969  Florio ................................. 128/92 B

FOREIGN PATENT DOCUMENTS 590,290   3/1925  France ................................... 128/92 D
960,010  10/1949  France ................................... 128/92 B
634,918   9/1936  Fed. Rep. of Germany ............. 128/83

Primary Examiner—Ronald L. Frinks
Attorney, Agent, or Firm—William R. Liberman

[57] ABSTRACT

A tie is provided for holding together the parts of a fractured bone. The tie includes an elongate, flexible, plastic strap provided on at least one face thereof with ratchet teeth and provided at one end thereof with an aperture through which the other end of the strap is capable of being passed. The aperture has a pawl adapted to engage the ratchet teeth. The strap is provided on that face which, when the end of the strap is passed through the said aperture, is the inner face, with at least one protrusion. Alternatively, to the use of protrusions on the strap, or in addition an elongate plate is positioned adjacent the fractured bone and straps are passed through slots in the plate. The plate then spaces from the bone.

13 Claims, 6 Drawing Figures

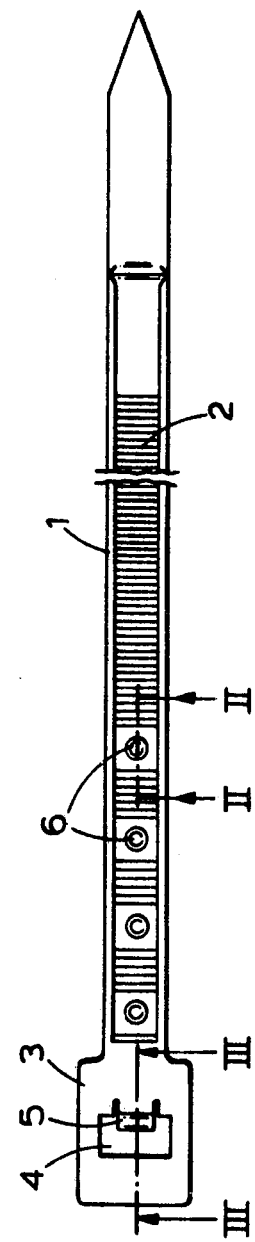
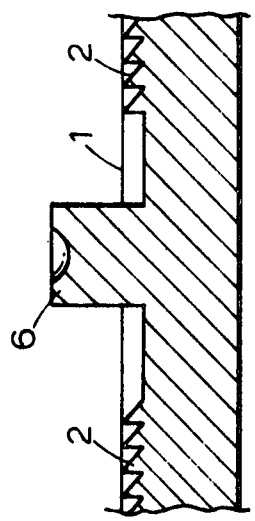
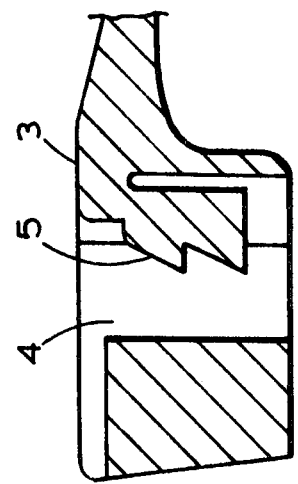

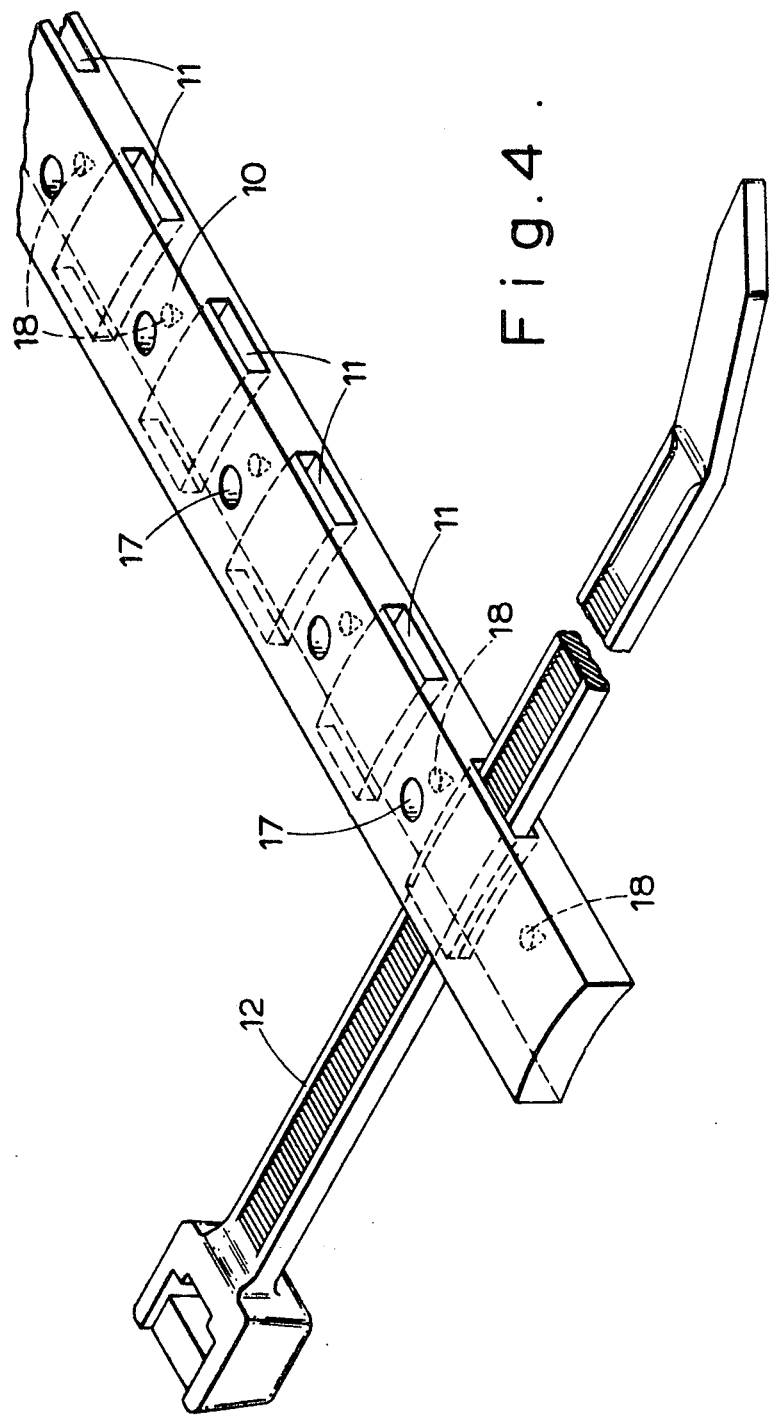

TIE FOR USE IN BONE FRACTURE SURGERY

This invention relates to a tie for use in orthopaedic surgery. Various methods are known for holding together parts of a fractured bone while healing of the bone takes place. Such methods include the use of a Kunschner nail which is inserted longitudinally through the centre of the fractured bone, and metal plates secured to the outside of the bone by screws. Such methods have, however, various disadvantages, and it is sometimes not possible to use them at all. For example a Kunschner nail cannot be used on the femur of patients fitted with an artificial metal hip joint, since the metal hip joint prevent the insertion of the nail.

The conventional method of holding together femur fractures where the patient has a metal hip joint has been to use a wire fixed around the femur. The use of such wire is very unsatisfactory as it cuts into the bone very severely and cuts off blood supply to the periosteum. Where such a wire is not used it has been general to treat patients on traction beds. Such patients often lie in bed for three to four months, and death as a result of complications arising from this immobilization is not uncommon.

It has been proposed (see U.S. Pat. No. 3,469,573) to use an annular metal band to fix bone fractures, such band being optionally provided with plastic studs. However, this proposal has numerous disadvantages, including the risk of studs falling out, the stiffness of the band which makes it difficult to place in position, and the awkwardness of the tensioning device provided for the band.

According to the present invention there is provided a device for holding together the parts of a fractured bone, comprising an elongate, flexible, plastic strap provided on at least one face thereof with ratchet teeth and provided on one end thereof with an aperture through which the other end of the strap is capable of being passed and which has a pawl adapted to engage the said ratchet teeth, and means for spacing the strap from the bone.

In the accompanying drawings:

FIG. 1 is a plan view of a first embodiment of the invention;

FIGS. 2 and 3 are sections on an enlarged scale through the embodiments of FIG. 1, taken on lines II—II and III—III respectively;

FIG. 4 shows a second embodiment of the invention; and

Figure 5:
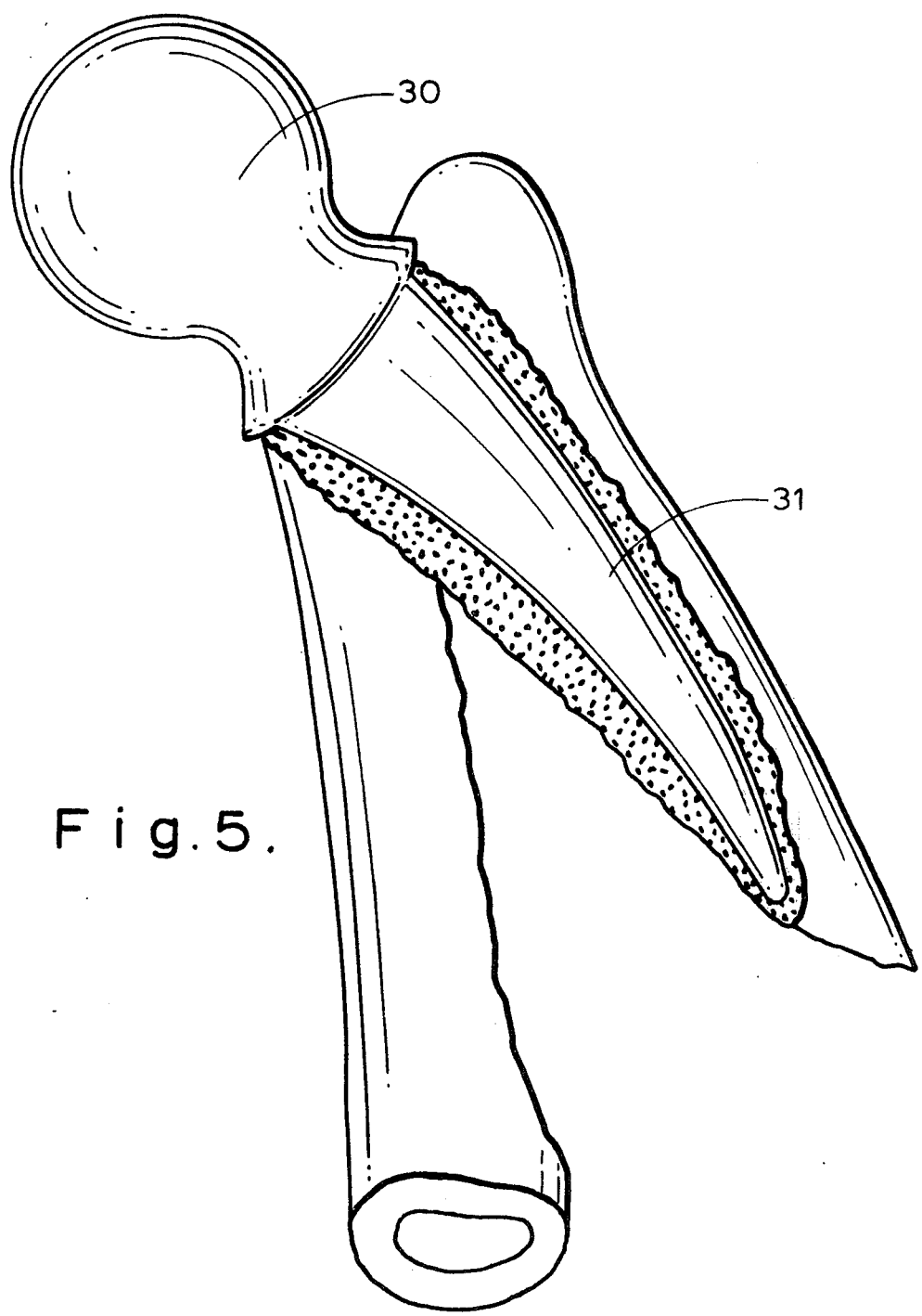
FIGS. 5 and 6 illustrate the application of the present invention to a femur fracture.

The embodiment shown in FIGS. 1 to 3 is in the form of a tie which comprises an elongate flexible strap 1 having ratchet teeth 2 on one face thereof. A widened portion 3 is provided at one end of the strap, the portion 3 containing a slot 4 of sufficient width to receive the strap 1 when the end of the strap is bent round and passed through the slot. Extending into the slot 4 is a tongue 5 which acts as a pawl engaging the ratchet teeth when the strap is passed through the slot to prevent withdrawal of the strap therefrom. The strap is provided on the same face as the teeth 2 with at least one protrusion or bump 6 integral therewith, four such protrusions being illustrated by way of example. The purpose of these protrusions is described below.

The tie is made predominantly of a plastic material, and is rendered opaque to X-rays. This may be done by including a radio-opaque filler, for example barium sulphate, in the plastics material or by including a radio-opaque object, for example a steel wire, within the plastics material. Whatever materials are used, the tie must be entirely of a physiologically acceptable material. One particularly suitable material is nylon-66 (polyhexamethylene adipamide). This material has been widely used in medical applications, for example in sutures, cannulae, tubing connectors, filters and semi-permeable membranes, and is known to by physiologically acceptable. Such a material implanted in the human body will undergo some loss in tensile strength, and research has indicated that a loss of the order of 10 to 15% over a period of several years can be expected. However, in view of the fact that the tie need only be operative for a period of the order of six weeks, this loss in strength can be ignored.

The tie can be used to hold together the parts of a fractured bone simply by passing it round the fracture, tightening it, and then cutting off any surplus length of strap. This will normally be sufficient in the case of a fracture which is not completely transverse. The protrusions 6 serve to space the strap from the bone, and this avoids any possibility of the blood supply to the bone being appreciably affected by the tie. The X-ray opacity of the tie enables the tie to be observed after it has been placed in position.

When the fracture involved is transverse a plurality of ties need to be used in conjunction with at least one plate which is positioned externally of the fracture and runs longitudinally of the bone. Such a plate 10 is shown in FIG. 4 of the accompanying drawings, from which it can be seen that the plate is provided with slots 11 through which ties 12 pass. The plate can also be conveniently made of a plastic material for example nylon-66, or it may be made of metal. The plate may be slightly curved in cross-section, as shown, to enable it to conform to the shape of the bone. The plate is provided with protrusions or studs 18, preferably integral with the plate, to space the plate from the bone.

The plate has apertures 17 formed therethrough to enable the plate to be screwed to the bone if this is desired. When used in conjunction with the plate the ties may not need to possess the protrusions 6, since the plate itself spaces the ties from the bone over at least part of the surface area of the bone.

Figure 6:
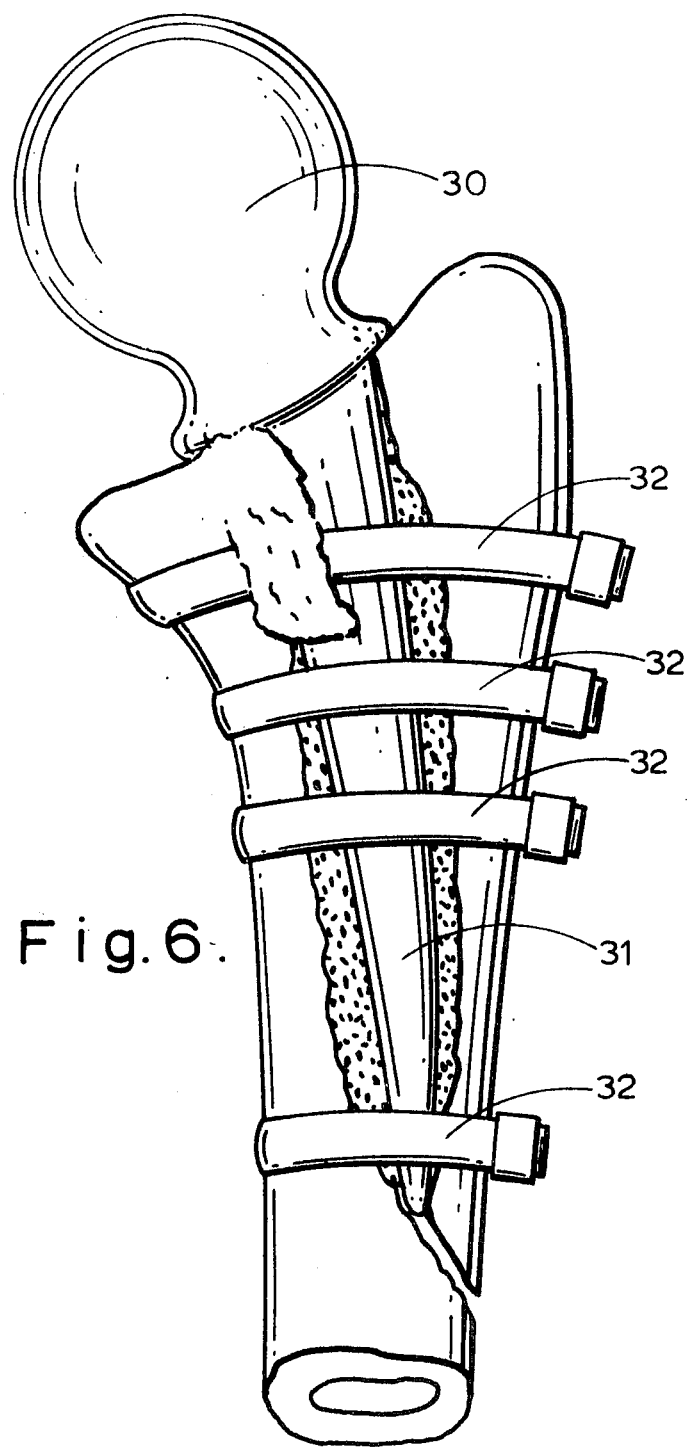

FIGS. 5 and 6 relate to the application of the present invention to an actual femur fracture which occurred to a woman aged 82. The woman had a metal joint which has been inserted after she had sustained a sub-capital fracture in the left hip joint. The femur fracture shown in FIG. 5 was an oblique spiral fracture in the region of the stem 31 of the hip joint. As shown by FIG. 6, the fracture was treated by passing four nylon ties, substantially the same structure as that shown in FIG. 1, around the bone. Each tie was inserted by passing a C-shaped copper tube around the bone, threading the tie onto one end of the tube and withdrawing the tube, taking the tie with it. Each tie took approximately one minute to insert. After the ties had been pulled tight the excess of the strap portion of each tie was cut off.

The patient was returned to bed and was able to lie free, i.e. not on traction. After two weeks the patient was able to get up and after three weeks was able to walk with the aid of a frame. The patient's hip was X-rayed at weekly intervals and this proved that there was no movement at the fracture site.

I claim:

1. A device for holding together the parts of a fractured bone, comprising an elongate, flexible, plastic strap provided on at least one face thereof with ratchet teeth and provided at one end thereof with an aperture through which the other end of the strap is capable of being passed and which has a pawl adapted to engage the said ratchet teeth, and means for spacing the strap from the bone.

2. A device according to claim 1, wherein the said spacing means are constituted by protrusions provided on and integral with that face which, when the said other end of the strap is passed through the said aperture, is the inner face.

3. A device according to claim 2, wherein the plastic material is nylon-66 (polyhexamethylene adipamide).

4. A device according to claim 1, wherein the plastic material is rendered opaque to X-rays by inclusion therein of a radio-opaque material.

5. A device according to claim 4, wherein the radio-opaque material is barium sulphate.

6. A device according to claim 4, wherein the radio-opaque material is in the form of an opaque object.

7. A device according to claim 1, wherein the spacing means is in the form of an elongate plate provided with a plurality of transversely extending slots of a size and shape to allow a corresponding plurality of plastic straps to pass therethrough, a plurality of protrusions being provided on that face of the plate which is to contact the bone.

8. A device according to claim 7, wherein the plastic material is nylon-66 (polyhexamethylene adipamide).

9. A device according to claim 7, wherein the plastic material is rendered opaque to X-rays by the inclusion therein of a radio-opaque material.

10. A device according to claim 9, wherein the radio-opaque material is barium sulphate.

11. A device according to claim 9, wherein the radio-opaque material is in the form of an opaque object.

12. A method of holding together the parts of a fractured bone comprising passing around the said parts at least one elongate, flexible, plastic strap having an aperture at one end thereof and provided on at least one face with ratchet teeth, the aperture being provided with a pawl, passing the other end of the strap through the said aperture so that the pawl engages the ratchet teeth, and continuing to pass the strap through the said aperture until the parts are securely held together, that face of the strap which is nearer the said parts being provided with protrusions which space the strap from the said parts.

13. A method of holding together the parts of a fractured bone, comprising positioning an elongate, plastic plate having a plurality of transverse slots therein adjacent the said parts, passing through each slot and around at least one of the said parts a respective elongate, flexible, plastic strap having an aperture at one end thereof and provided on at least one face with ratchet teeth, the aperture being provided with a pawl, passing the other end of each strap through the said aperture so that the pawl engages the ratchet teeth, and continuing to pass the strap through the said aperture until the parts are securely held together.

* * * * *